US00PP29050P2

(12) United States Plant Patent
Bradford et al.

(10) Patent No.: US PP29,050 P2
(45) Date of Patent: Mar. 6, 2018

(54) PLUM TREE NAMED 'PLUMCANDY XI'

(50) Latin Name: *Prunus salicina*
Varietal Denomination: Plumcandy XI

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 15/530,227

(22) Filed: Dec. 15, 2016

(51) Int. Cl.
*A01H 5/08* (2006.01)

(52) U.S. Cl.
USPC ..... Plt./184

(58) Field of Classification Search
USPC ..... Plt./184
See application file for complete search history.

(56) References Cited

U.S. PATENT DOCUMENTS

PP14,220 P2 10/2003 Bradford
PP19,527 P2 12/2008 Bradford

*Primary Examiner* — Annette H Para

(57) ABSTRACT

The present invention relates to a plum tree and more particularly to a new and distinct variety broadly characterized by a medium size, moderately vigorous, hardy, and productive tree. Being self-unfruitful, the present variety requires cross pollination from another plum or interspecific tree that blooms during the late season, such as 'Plumsweet XVI' interspecific tree (U.S. Plant Pat. No. 26,055). The present variety's moderate abundance of blossoms and pollen entices strong bee activity to facilitate pollination. The fruit matures under the ecological conditions described during early September, with first picking on Sep. 8, 2016. However, the fruit has been observed to hang firm on the tree for up to five weeks. The fruit is uniform, large in size, nearly full red in skin color, clingstone in type, pure orange yellow in flesh color, firm in texture, juicy, and very good in flavor.

1 Drawing Sheet

Botanical classification: *Prunus salicina.*
Variety denomination: 'PLUMCANDY XI'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree, which has been denominated varietally as 'Plumcandy XI'.

During a typical blooming season we isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2007 one such house containing 'Black Majesty' plum tree (U.S. Plant Pat. No. 19,527) was crossed by us in this manner. To pollinate this plum tree, we selected bouquets from several sources of plum trees without keeping specific written details. Upon reaching maturity the fruit from this plum tree was harvested, and the seeds were removed, cracked, stratified and germinated as a group with the label "H21". They were grown as seedlings on their own root in our greenhouse and upon reaching dormancy transplanted to a cultivated area of our experimental orchard located near Le Grand, Calif. in Merced County (San Joaquin Valley). During the summer of 2013 the claimed variety was selected by us as a single plant from the group of seedlings described above. Subsequent to origination of the present variety of plum tree, we asexually reproduced it by budding and grafting in the experimental orchard described above, and such reproductions were true to the original tree in all respects. The reproduction of the variety included the use of 'Nemaguard' (unpatented) rootstock upon which the present variety was compatible and true to type.

The present variety is similar to its seed parent, 'Black Majesty' (U.S. Plant Pat. No. 19,527) plum by having a medium size and productive tree, by being self-unfruitful, and by producing plums that are very sweet in flavor, full yellow in flesh color, juicy, and firm in texture, but is distinguished therefrom by blooming later in the season and by producing plums that are much larger in size, that are red instead of mostly black in skin color, that are oblate instead of globose in shape, and that ripen at least two weeks later.

The present variety is most similar to its seed parent, 'September Yummy' (U.S. Plant Pat. No. 14,220) plum by having a productive tree, by being self-unfruitful, and by producing plums that ripen in early September and that are nearly full red in skin color, nearly full yellow in flesh color, very good in flavor, juicy, and firm in texture, but is distinguished therefrom by having a somewhat smaller tree, by blooming later in the season, and by producing plums that are larger in size, somewhat oblate instead of globose in shape, sweeter, and clingstone instead of semi-freestone.

SUMMARY OF VARIETY

The present plum variety is characterized by a medium size, moderately vigorous, hardy, and productive tree. Being self-unfruitful, the present variety requires cross pollination from another plum or interspecific tree that blooms during the late season, such as 'Plumsweet XVI' interspecific tree (U.S. Plant Pat. No. 26,055). The present variety's moderate abundance of blossoms and pollen entices strong bee activity to facilitate pollination. The fruit matures under the ecological conditions described during early September, with first picking on Sep. 8, 2016. However, the fruit has been observed to hang firm on the tree for up to five weeks. The fruit is uniform, large in size, nearly full red in skin color, clingstone in type, pure orange yellow in flesh color, firm in texture, juicy, and very good in flavor.

DRAWING

The accompanying photograph exhibits four whole fruits positioned to display the characteristics of the skin color and form, one divided fruit to reveal the flesh, a typical stone, typical leaves, and an inset depicting flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif., and was developed at the state of firm ripe on Sep. 25, 2016, on the original tree during its ninth growing season. All major color code designations are by reference to the Inter-Society Color Council, National Bureau of Standards. Common color names are also used occasionally.

It is to be noted that the 2016 fruit season in California was very warm during the spring and the ripening times of almost all varieties were about fourteen days earlier than other years.

TREE

Size: Medium, reaching and maintaining a height of 10' [3.05 m.] and a spread of 7' [2.13 m.] after nine growing seasons utilizing typical dormant pruning.

Vigor: Medium vigor, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Pruned to a vase form.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Productive, thinning usually necessary.

Fertility: Self-unfruitful, requiring cross pollination by a suitable mid to late seasonal blooming plum or interspecific, such as 'Plumsweet XVI' interspecific tree (U.S. Plant Pat. No. 26,055).

Bearing: Regular bearer, weather dependent, no crop failures observed as of yet.

Trunk:

*Size*.—Medium, reaching a maximum diameter of 3" [76.2 mm.] after the ninth growing season.

*Texture*.—Medium, shaggy.

*Bark color*.—A Light grayish brown [60. l.gy.Br] and Light brownish gray [63. l.brGy] variegation with Brownish orange [54. brO] crevices present.

*Lenticels*.—Approximate Number Per Square Inch: 10. Color: Strong yellowish brown [74. s.yBr]. Typical Size: ⅛" [3.2 mm.] in length. The width is typically one fourth as much as the length. Shape: Eye-shaped.

Branches:

*Size*.—Medium, scaffold diameter is 1½" [38.1 mm.] measured 12" above the crotch, limb diameter is 1¼" [31.8 mm.] measured 12" above the first fork.

*Texture*.—Smooth on first and second year wood, increasing roughness with age.

*Color*.—1st Year Wood Topside: Grayish red [19. gy.R]. 1st Year Wood Underside: Brilliant yellow green [116. brill.YG]. Older Wood: A Light brownish gray [63. l.brGy] and Grayish brown [61. gy.Br] variegation with Light yellowish brown [76. l.yBr] crevices present.

*Lenticels*.—Approximate Number Per Square Inch: 60. Color: Light grayish yellowish brown [79. l.gy.yDr]. Typical size: Small, 1/64" [0.4 mm.] in length. The width is typically one fourth as much as the length. Shape: Rectangular.

Leaves:

*Size*.—Medium. Average Length: 3¼" [82.6 mm.]. Average width: 1⅝" [41.3 mm.].

*Arrangement*.—Alternate.

*Thickness*.—Medium.

*Form*.—Elliptical.

*Apex*.—Acuminate.

*Base*.—Acute with an average angle base angle of seventy-five degrees.

*Surface*.—Smooth.

*Color*.—Dorsal Surface: Moderate olive green [125. m.OlG]. Ventral Surface: Moderate yellow green [120. m.YG].

*Margin*.—Finely serrate.

*Venation*.—Pinnately net veined.

*Petiole*.—Average Length: ½" [12.7 mm.]. Average Thickness: 1/16" [1.6 mm.]. Color: Moderate greenish yellow [102. m.gY] with Grayish purplish red [262. gy.pR] areas where exposed to sunlight.

*Stipules*.—Number: 2 per leaf, up to 6 per growing tip. Average Length: ⅜" [9.5 mm.]. Color: Moderate yellow green [120. m.YG] becoming Dark grayish reddish brown [47. d.gy.rBr] with age.

*Glands*.—Number: 1 to 4, most often 2. Position: Usually opposite, positioned at the intersection of petiole and leaf blade. Form: Globose. Size: Small, 1/64" [0.4 mm.] in diameter. Color: Moderate yellow green [120. m.YG] becoming Dark grayish reddish brown [47. d.gy.rBr] in the center with age.

*Leaf buds*.—Medium, pointed.

Flower buds:

*Hardiness*.—Hardy, with respect to central California blooming season.

*Diameter*.—Typically 3/16" [4.8 mm.] 1 week before bloom.

*Length*.—Typically ⅜" [9.5 mm.] 1 week before bloom.

*Form*.—Free, not touching.

*Surface*.—Non-pubescent.

*Color*.—White [263. White].

Flowers: Perfect, complete, perigynous, usually a single pistil, about twenty-eight stamens, five sepals and petal locations alternately positioned.

*Average flower diameter.*—1 1/16" [27.0 mm.].
*Average flower depth.*—3/8" [9.5 mm.] when fully open.
*Number of petals.*—Five, no double blossoms observed.
*Petal shape.*—Oval.
*Petal margin.*—Entire, somewhat wavy.
*Petal arrangement.*—Overlapping.
*Average petal diameter.*—1/2" [12.7 mm.].
*Average petal length.*—9/16" [14.3 mm.].
*Petal apex.*—Rounded.
*Petal base.*—Rounded.
*Petal color.*—White [263. White] on both sides.
*Anther color.*—Light yellow [86. l.Y].
*Pollen production.*—Moderate, bee enticing.
*Stigma color.*—Light greenish yellow [101. l.gY].
*Stigma position.*—Stigma is located slightly above the surrounding anthers.
*Stamen position.*—Typically located about 1/32" [0.8 mm] below the petals.
*Sepal color.*—Light yellow green [119. l.YG] on both sides.
*Sepal length.*—5/32" [4.0 mm.].
*Sepal width.*—5/32" [4.0 mm.].
*Average pistil length.*—1/2" [12.7 mm.].
*Average stamen length.*—7/16" [11.1 mm.].
*Ovary.*—Smooth.
*Fragrance.*—Moderate.
*Blooming period.*—Late compared to other varieties, about 6 days after 'September Yummy' plum (U.S. Plant Pat. No. 14,220).
*Onset of bloom.*—One percent on Feb. 19, 2016.
*Date of full bloom.*—Feb. 28, 2016.
*Duration of bloom.*—One to two weeks, dependent on ambient temperature.
*Bloom density.*—Moderate.
*Number per cluster.*—Typically 3 to 5, up to 8 observed.

FRUIT

Maturity when described: Firm ripe, Sep. 25, 2016.
Date of first picking: Sep. 8, 2016.
Date of last picking: Oct. 10, 2016.
Size: Uniform, large.

*Average diameter across axially.*—2 1/2" [63.5 mm.].
*Average diameter suture plane.*—2 3/4" [69.9 mm.].
*Average diameter across cheek plain.*—2 11/16" [68.3 mm.].
*Typical weight.*—6.9 ounces [196 grams].

Form: Uniform, oblate, slightly asymmetrical, compressed axially.

*Longitudinal section from.*—Round to somewhat oblate.
*Transverse section through diameter.*—Round.

Suture: A very shallow trough extending from the base to the apex.
Ventral surface: Rounded, lipped on both sides.
Lips: Slightly unequal.
Cavity: Flaring, circular, suture showing on one side.

*Depth.*—1/2" [12.7 mm.].
*Breadth.*—7/8" [22.2 mm.].

Base: Truncate, slightly cordate when viewed parallel to the suture.
Apex: Rounded.
Pistil point: A Light orange yellow [70. l.OY] inconspicuous dot.
Stem: Medium size.

*Average length.*—7/16" [11.1 mm.].
*Average width.*—1/16" [1.6 mm.].

Skin:

*Thickness.*—Medium.
*Surface.*—Smooth.
*Tenacity.*—Tenacious to flesh.
*Astringency.*—Slight.
*Tendency to crack.*—None observed.
*Color.*—Very deep red [14. v.deep R] over a Strong red [12. s.R] background with moderate Brilliant orange yellow [67. brill.OY] freckling throughout.

Flesh:

*Color.*—Light orange yellow [70. l.OY] closer to the pit, becoming Brilliant orange yellow [67. brill.OY] closer to the skin with Pale orange yellow [73. p.OY] fibers throughout.
*Surface of pit cavity.*—Covered with Brilliant orange yellow [67. brill.OY] fibers.
*Amygdalin.*—Scarce.
*Juice.*—Abundant, rich.
*Texture.*—Firm, crisp.
*Fibers.*—Fine, tender.
*Ripens.*—Fairly even, slightly earliest on the shoulder.
*Flavor.*—A tasty blend of acid and sugar, typically 23-24 brix.
*Aroma.*—Very slight.
*Eating quality.*—Very good.

STONE

Type: Clingstone.
Form: Oval.
Hilum: Narrow.
Base: Rounded.
Apex: Acute with an average angle of 75 degrees and a sharp tip 1/16" [1.6 mm.] in length.
Sides: Slightly unequal.
Surface: Rough.
External color of stone: Dark orange yellow [72. d.OY].
Pit wall color when cracked: Moderate yellowish brown [77. m.yBr].
Cavity surface color: Light yellowish brown [76. l.yBr].
Average pit wall thickness: 1/16" [1.6 mm.]
Average length: 15/16" [23.8 mm.].
Average width: 11/16" [17.5 mm.].
Average breadth: 5/16" [7.9 mm.].
Tendency to split: None observed.
Kernel:

*Form.*—Oval.
*Pellicle color.*—Dark yellowish brown [78. d.yBr].
*Skin color.*—Strong yellowish brown [74. s.yBr].
*Vein color.*—Deep yellowish brown [75. deep yBr].
*Taste.*—Bitter.
*Viable.*—Yes.
*Average length.*—9/16" [14.3 mm.].
*Average width.*—3/16" [4.8 mm.].

USE

Market: Fresh market and long distance shipping.

Keeping quality: Excellent. Fruit quality observed to remain in good condition after 30 days in standard cold room at 36° Fahrenheit [2° Celsius].

Shipping quality: Excellent.

Resistance to insects: No unusual susceptibilities noted.

Resistance to diseases: No unusual susceptibilities noted.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *prunus salicina*, substantially as illustrated and described, that is most similar to its seed parent, 'September Yummy' (U.S. Plant Pat. No. 14,220) plum by having a productive tree, by being self-unfruitful, and by producing plums that ripen in early September and that are nearly full red in skin color, nearly full yellow in flesh color, very good in flavor, juicy, and firm in texture, but is distinguished therefrom by having a somewhat smaller tree, by blooming later in the season, and by producing plums that are larger in size, somewhat oblate instead of globose in shape, sweeter, and clingstone instead of semi-freestone.

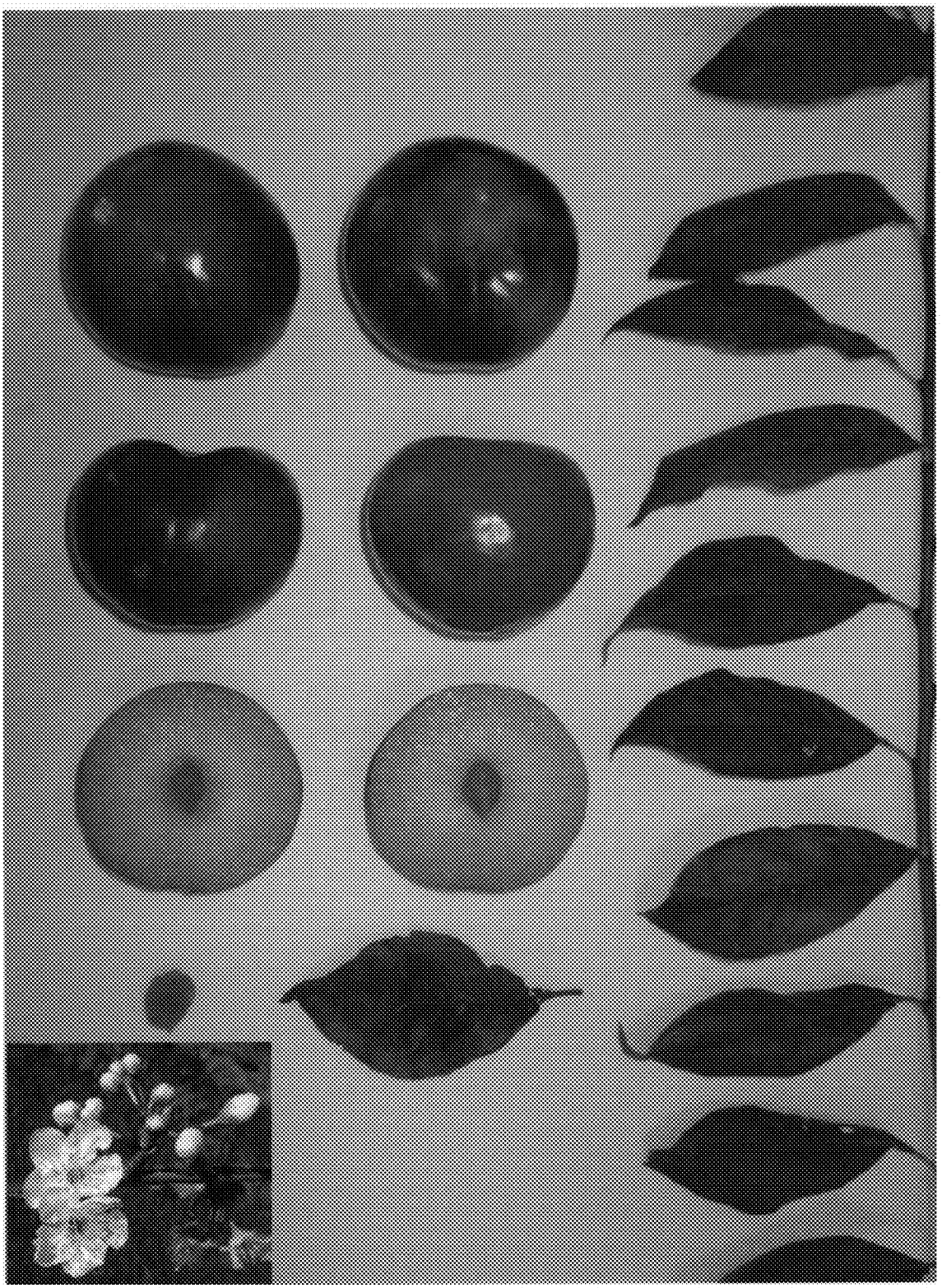

* * * * *